United States Patent [19]
Kishi et al.

[11] Patent Number: 5,804,140
[45] Date of Patent: Sep. 8, 1998

[54] CORROSION INSPECTION PLATE, MEASUREMENT FOR CORROSIVE ENVIRONMENT AND CASE FOR THE CORROSION INSPECTION PLATE

[75] Inventors: Tadashi Kishi; Xinmin Xu; Nobuteru Sawayama, all of Tokyo, Japan

[73] Assignee: Yokogawa Engineering Service Corporation, Tokyo, Japan

[21] Appl. No.: 934,949

[22] Filed: Sep. 22, 1997

Related U.S. Application Data

[63] Continuation of Ser. No. 573,475, Dec. 15, 1995, abandoned.

[30]  Foreign Application Priority Data

Dec. 20, 1994 [JP] Japan .................................. 6-316779

[51] Int. Cl.$^6$ .................................................. G01N 17/00
[52] U.S. Cl. .............................. 422/53; 436/6; 437/180; 437/187; 73/61.62; 73/86
[58] Field of Search .................. 436/6; 437/187, 437/180, 203; 73/86, 61.62, 104; 422/53

[56]  References Cited

U.S. PATENT DOCUMENTS

| | | | |
|---|---|---|---|
| 2,351,644 | 6/1944 | Talley et al. | 422/53 |
| 3,124,771 | 3/1964 | Rohrback | 422/53 X |
| 3,573,570 | 4/1971 | Fuller et al. | 317/235 |
| 4,012,756 | 3/1977 | Chaudhari et al. | 357/5 |
| 4,217,544 | 8/1980 | Schmidt | 436/6 X |
| 4,278,508 | 7/1981 | White et al. | 204/1 T |
| 5,274,270 | 12/1993 | Tuckerman | 257/758 |
| 5,372,849 | 12/1994 | McCormick et al. | 427/253 |
| 5,411,890 | 5/1995 | Falat | 436/6 |
| 5,466,605 | 11/1995 | Glaunsinger et al. | 436/6 |
| 5,547,907 | 8/1996 | Rohner | 437/187 |

*Primary Examiner*—Harold Y. Pyon
*Attorney, Agent, or Firm*—Moonray Kojima

[57]  ABSTRACT

An apparatus for measuring the amount of various corrosive gases present in a corrosive environment, which uses a metal plate having a thin metalic film thereon formed by sputtering or deposition, instead of the conventional hand made metal sheet, and which measures the thickness of a corrosion film formed on the metal film by utilizing an X-ray spectrum instead of the conventional cathode reduction method, and without destroying the corrosion film, through use of a calibration curve. The invention also provides a novel casing for holding the metal plate in the corrosive environment during measurement.

5 Claims, 10 Drawing Sheets

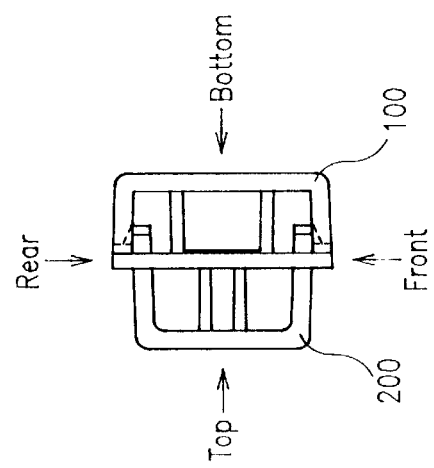
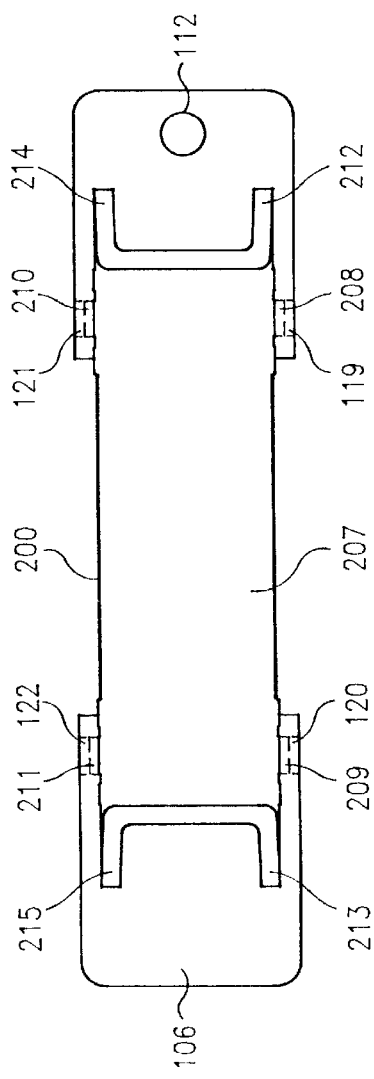
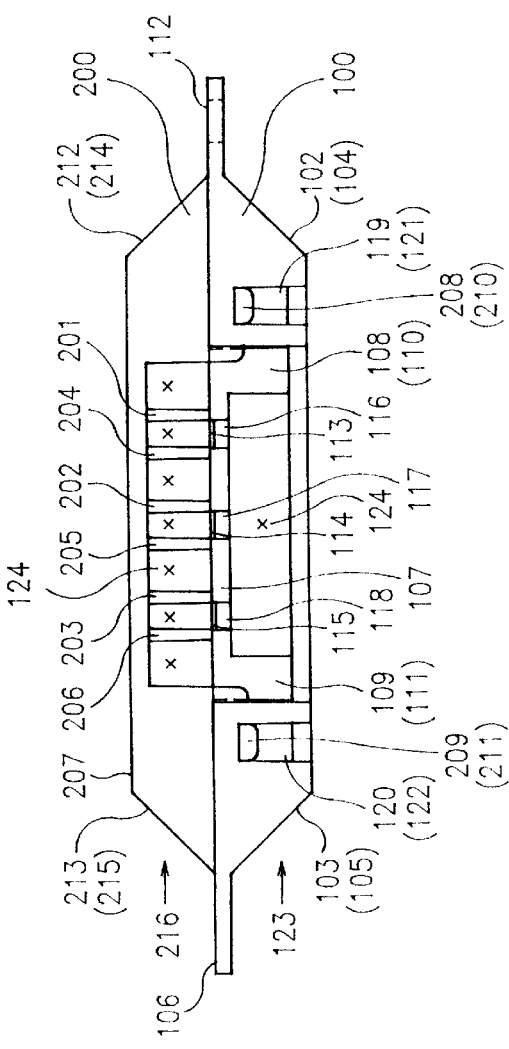

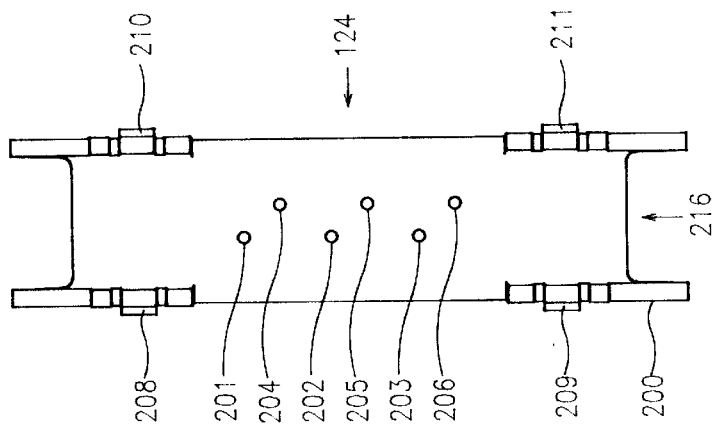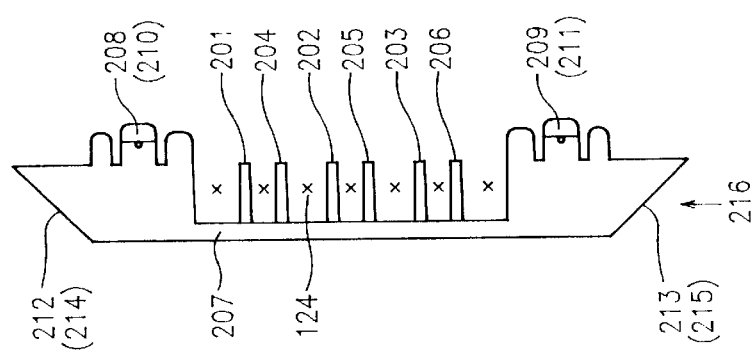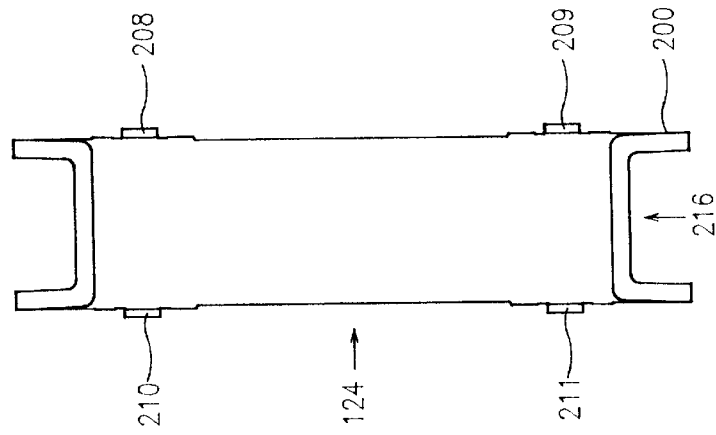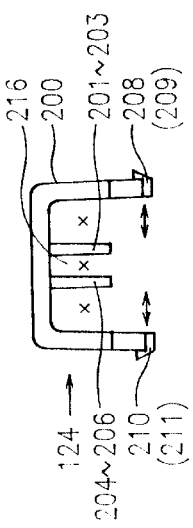

CORROSION INSPECTION PLATE, MEASUREMENT FOR CORROSIVE ENVIRONMENT AND CASE FOR THE CORROSION INSPECTION PLATE

This is a continuation of Ser. No. 08/573,475 filed Dec. 15, 1995, now abandoned.

BACKGROUND OF THE INVENTION

1. Field of Invention

This invention relates to method and apparatus for measurement of a corrosive atmospheric environment; and more particularly, to such method and apparatus using an inspection plate and also to a casing for holding the inspection plate.

2. Description of the Prior Art.

In order to survey environmental air pollution or to predict deterioration of various equipment and installations, such as computers, due to corrosion, a method has been employed in the art for measuring corrosive gases by exposing a plate (called "inspection plate") made, for example of copper, silver, or the like, to a corrosive environment for a predetermined period, such as one month, and then, measuring the thickness of the corrosion film which is formed on the plate. This measurement method is known as the "cathode reduction method", and is the basis of the ISA standard ISA-S71.04-1985. This method uses a metal sheet, 15 cm$^2$ (i.e.nominal value) in size, cut from a sheet of highly conductive, oxygen-free (e.g. 99.9% pure) copper which is 0.635mm thick. The plate is exposed to the corrosive environment for one month, and then the accumulated corrosion film on the surface thereof is measured by electrolysis technique wherein the plate is immersed in a KCl solution and by using a platinum rod as one electrode and the plate serving as the other electrode, electricity is passed between the two electrode and the voltage therebetween is measured. The composition of the corrosion film is determined by the voltage measurement, and thickness of the film is determined by the lapse of time between the start of the procedure and the fall of voltage.

In general, the corrosive environment is classified as to the degree of corrosion G1, G2, G3, GX, on the basis of the measured thickness of the corrosion film formed on the inspection plate. These degrees or levels of corrosion are defined as follows:

(1) G1 is the level at which the corrosion does not affect the service life of the equipment, This is indicated by the thickness of corrosion film being less than 300 Å.
(2) G2 is the level at which the corrosion does affect the service life of the equipment. This is indicated by the thickness of the corrosion film being between 300 to 1000 Å.
(3) G3 is the level at which the corrosion severely affects the service life of the equipment. This is indicated by the thickness of the corrosion film being between 1,000 to 2,000 Å.
(4) GX is the level at which the corrosion is so severe that only equipment which are provided with protection against corrosion, can be used. This is indicated by the thickness of the corrosion film being more than 2,000 Å.

These and other particulars are set forth in ISAA-S71.04-1985, entitled "Environmental Conditions for Measurement and Control Systems: Airborne Contaminants".

FIG. 1 shows a sectional view of a conventional inspection plate 6, made for example of a metal, such as copper or silver or the like, and wherein after exposure to corrosive gases, the surface thereof is corroded, and is used to carry out the conventional "cathode reduction method" of measurement of the corrosive gases. The inspection plate 6, which may be of copper, is hand finished with sand paper or the like to a desired degree of fineness of surface, and prior to use as the inspection plate which is exposed to the corrosive gases.

It is apparent that both the roughness and area of the finished surface should be large. Consequently, the use of metal plate 6, having different degrees of surface finish, due to the use of hand finishing, may result in errors of measurement.

Corrosion film 7 which is formed on the surface of the copper (Cu) plate 6 upon exposure to the corrosive environment will be copper oxide ($Cu_2O$), copper sulfide ($Cu_2S$), copper chloride ($CuCl_2$), etc depending on the composition of the corrosive environment. The corrosion film 7 which is formed when the plate 6 is made of silver (Ag) will be silver sulfide ($Ag_2S$), silver chloride (AgCl), etc. Carbon film 8 is formed on the surface of corrosion film 7 in a normal corrosive environment.

In measurements obtained using metal plates 6 having a variety of different surface finish, the auger analysis method may be used, wherein the measurement is made by first etching the corrosion film, and measuring the etched location. Even this type of measurement results in inaccuracies.

One problem with the above discussed "cathode reduction method" is that it is difficult to perform measurement on a large number of test samples because it takes almost one hour to complete the measurement of each test sample. Also, the metal plate 6 which is approximately 15 cm$^2$ in size is suspended in the corrosive environment; hence, the method of suspension may vary and affect the result so that uniformity of measurement suffers.

Another prior art type of measurement is disclosed in U.S. Pat. No. 5,208,162, but, this method and apparatus has its own set of problems.

SUMMARY OF THE INVENTION

Accordingly, an object of the invention is to overcome the aforementioned and other deficiencies and disadvantages of the prior art.

Another object is to provide a more accurate measurement of the thickness of a corrosion film formed in a corrosive environment and to do so in a shorter period of time.

The foregoing and other objects, features and advantages are attained in the invention, by improving the inspection plate by forming a thin metal film thereon by using a of sputtering or vacuum deposition technique, instead of the use of the conventional hand made surface plate, and by using the X-ray spectrum with calibration curves to prevent the corrosion film from being destroyed, instead of the use of the conventional cathode reduction method.

In another aspect of the invention, a casing is provided wherein secure stable ventilation is obtained even when a small inspection plate is used, and which protects the plate from direct contact with falling dust and moisture, and furthermore, provides easy and secure installation and removal.

The inspection plate comprises a thin metal film which is formed by a sputtering or deposition technique, over a substantially flat substrate, made, for example of silicon. The thin metal film is finished in such a manner as to maintain a surface roughness thereof which is constant and less than the thickness of the thin metal film. It is preferably 10% or less than the thickness of the thin metal film. That is to say, the degree of fineness of the surface of the thin metal film is such as to be a mirror finish, in some cases. The thin metal film, which may be made of copper or silver, or like metal, and having such surface finish is exposed to a corrosive environment. The different gases therein will react with the thin metal film to form a corrosion surface which may be of a compound or compounds of such gases and metal in the thin metal film. The corrosion film is then measured in the manner discussed below. The corrosion film could be, for example, Copper sulfide, if the thin metal film is of copper, and a gas in the corrosive environment is sulfur.

The corrosion film is measured by quantitative analysis using an X-ray microanalyzer, wherein an electron beam of the X-ray microanalyzer is accelerated to a desired level in order to obtain the desired level of sensitivity to oxygen and carbon, or other elements. A high voltage generating circuit is used to accelerate the electron beam. The thickness of the corrosion film is scanned by the electron beam and appropriate detection of the results of the scans is made and processed.

Moreover, the invention provides a casing for holding the the inspection plate and comprises a base, which accommodates the inspection plate, and a cover which is engaged with the base to form the casing unit. The casing provides a plurality of supports for the plate and bars to hold the plate. The cover is pressed into the base to secure the base and plate.

BRIEF DESCRIPTION OF THE DRAWINGS

FIG. 9 is an assembly drawing depicting a front view of an illustrative casing for the inspection plate.

FIG. 10 is a side view depicting the front, rear, top and bottom viewing directions of the casing of FIG. 9.

FIG. 11 is a top view depicting the illustrative casing.

FIG. 18 is a front view depicting the cover of the illustrative casing.

FIG. 19 is a top view depicting the cover of the illustrative casing.

FIG. 20 is a side view depicting the cover of the illustrative casing.

FIG. 21 is a bottom view depicting the cover of the illustrative casing.

DETAILED DESCRIPTION OF THE PREFERRED EMBODIMENTS

Figure 1:
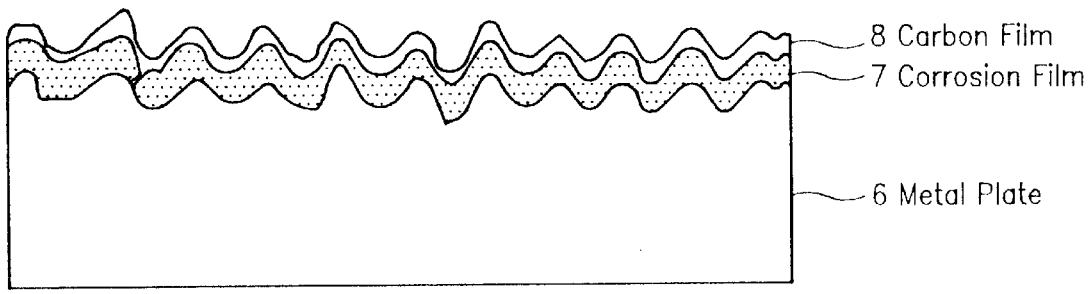
FIG. 1 is a cross sectional view depicting a conventional hand made inspection plate.
Figure 2:
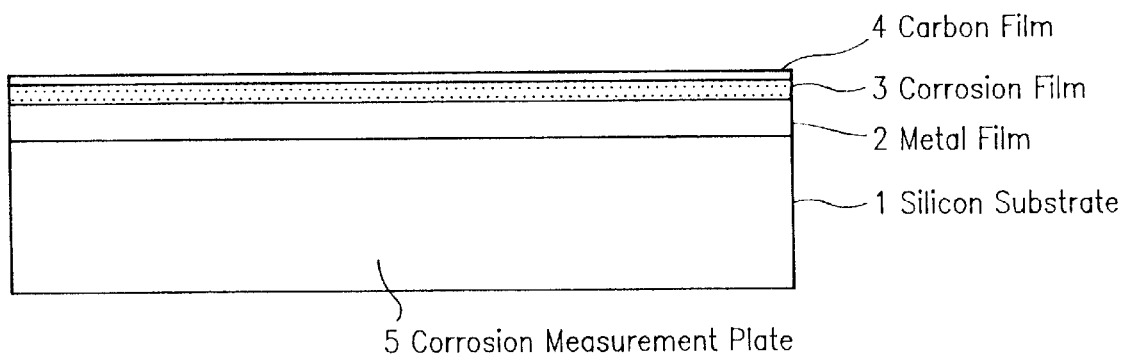
FIG. 2 is a cross sectional view depicting an illustrative embodiment of the invention comprising the invention inspection plate.

FIG. 2 shows the cross section of inspection plate 5 comprising a silicon substrate 1, upon which a thin metal film 2 is formed by sputtering or vacuum deposition, or like method. When the plate is exposed to a corrosive environment, there is formed on the exposed surface of the thin metal film 2, a corrosion film 3, and on top of that film, a carbon film 4. The inspection plate 5 is fabricated as follows. A silicon substrate 1, for example of the p-type, and having a specific resistance of 4 to 20 cm, and also having a surface which is substantially flat, is used. Measurement with an atomic force microscope shows that the flatness of the silicon substrate having an area of 100 $\mu m^2$, when the silicon substrate usually used for the manufacture of integrated circuits is used, the flatness is about 1.4 Å. A thin film 2 is formed, for example, of copper, silver, or the like by forming a thin film of such metal on the surface of the silicon substrate by using a sputtering or deposition process. Thin metal film 2 is preferably finished so that the thickness thereof is at least 2000 Å, and the surface roughness is obtained of about 200 Å. The type of metal used for the thin film 2, e.g. copper or silver, etc, is selected depending on the measuring corrosive environment.

The film thickness of 2000 Å, mentioned above is utilized so as to conform to the indicated standard ISA-S71.04-1985. Such thickness of the thin metal film 2 is required so as to measure the corrosive environment level GX, that is to form a corrosion film of a thickness of 2,000 Å after one month exposure. If the desired standard is different, the film thickness can be altered accordingly.

The surface roughness of 200 Å is found to be preferable and is determined to be about 10% of the thin metal thickness, of in this case 2000 Å. As the percentage becomes smaller than the 10%, (that is to say that the surface roughness becomes smoother), the dispersion of measured values for different inspection plates can be reduced.

When sputtering is used to form the thin metal film 2 on silicon substrate 1, the heating temperature of the silicon substrate 1 is suitably controlled to prevent formation of larger metal particles than desired to form the desired surface roughness of the thin film 2. When a metal having poor adhesion to silicon, such as copper, is used to form the thin metal film 2 by sputtering on silicon substrate 1, silicon oxides formed on the substrate surface is removed, e.g. by inverse sputtering, prior to the sputtering step to improve adhesion of the metal to the silicon. Then, chips each being about 7×7 $mm^2$ in size, are cut to form the inspection plate 5. The inspection plate 5 thus produced is referred to as a silicon substrate corrosion inspection plate.

The corrosion film 3 comprises compounds formed by reaction between the metal of the film 3 and the gases present in the corrosion environment. For example, if the thin metal film is of Cu or Ag, and various gases such as oxygen, sulfur, chlorine, etc, the following compounds will form the corrosion film 3. Copper oxide ($Cu_2O$), copper sulfide ($Cu_2S$), copper chloride ($CuCl_2$), silver chloride (AgCl), silver sulfide ($Ag_2S$), etc.

A carbon film 4 normally is formed on the surface of the corrosion film 3 when inspection plate 5 is exposed to the environment.

Figure 3:
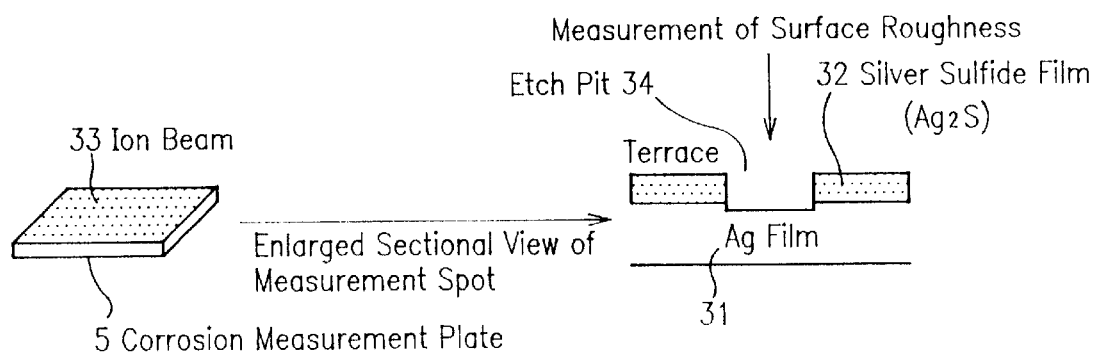
FIG. 3 is an explanatory drawing depicting measurement of the thickness of a silver sulfide film formed over a thin silver film using a secondary ion analyzer.

The thickness of the corrosion film 3 on plate 5 is measured by using a secondary ion mass spectrometer (also called herein "SIMS"), which is calibrated with a surface roughness tester. FIG. 3 shows how to measure the thickness of film 3, which may be of silver sulfide formed on a silver thin film 2, for example. The surface of the silver sulfide film 32 is etched to a depth at which film 32 interfaces with silver film 31, using an ion beam 33 from SIMS 33, as will be discussed further hereinbelow. The depth of the created etch pit 34 is measured directly with a probe of a surface roughness meter.

Figure 4:
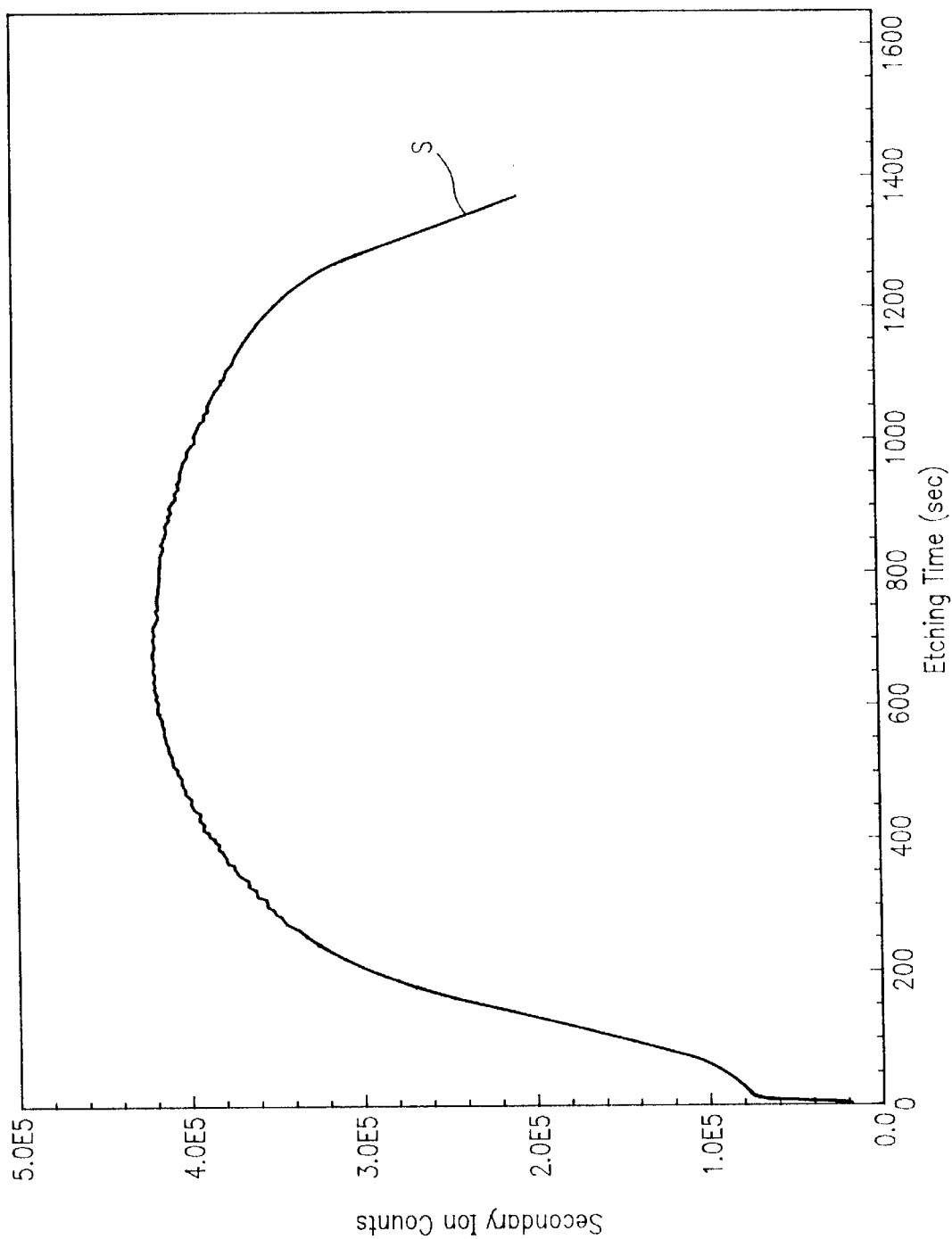
FIG. 4 shows a graph depicting depth profile created by a secondary ion mass spectrometer.

FIG. 4 shows the depth profile obtained by measuring the secondary ions of sulfur (in the case when silver sulfide is formed, for example), while etching the corrosion film with SIMS 33. The SIMS method is performed by counting the number of sulfur ions emitted as secondary ions from sulfur within silver sulfide film 32, as a result of an ion beam irradiated from SIMS over sulfide film 32. (See FIG. 3). In FIG. 4, the ordinate represents the secondary ion count and the abscissa represents the etching time in seconds. The number of sulfur ions are counted from the start of etching at the surface of the silver sulfide film by means of the SIMS to the time the ion count reaches a peak value. When the etching reaches the silver film 31 in FIG. 3, the count of the sulfur ion becomes substantially zero. When the ion count becomes half of the maximum value, the etching is stopped. Then, the depth of etch pit 34 in FIG. 3 is directly measured with a probe of the surface roughness meter. In this manner, the silver sulfide film 32 is identified by means of the SIMS as a compound of sulfur produced on the surface of the inspection plate 5, and is measured as to the thickness thereof. In a similar manner, the thickness of films formed of a compound of chlorine or other elements, are measured.

Figure 5:
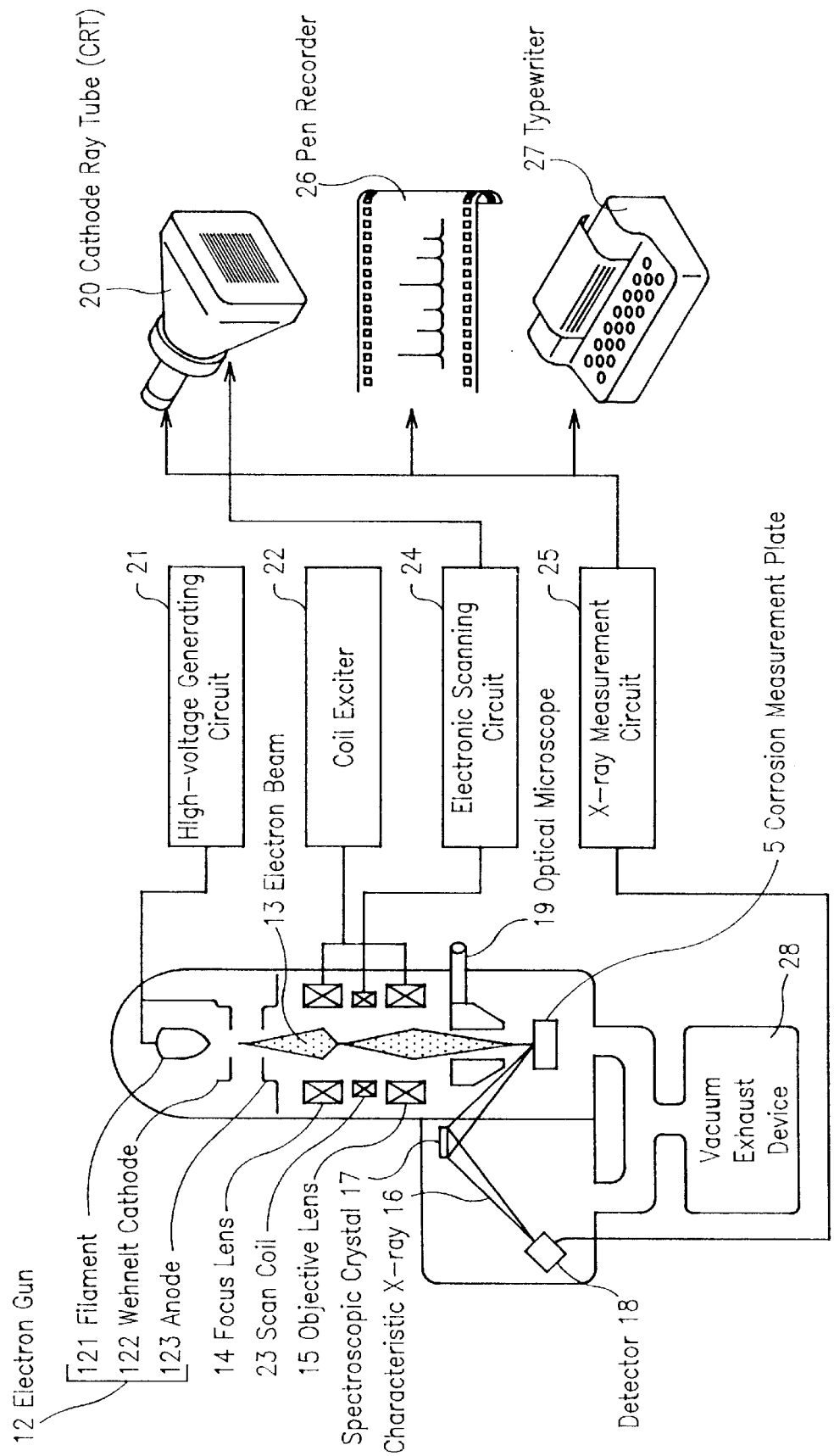
FIG. 5 is an explanatory drawing depicting an X-ray micro-analyzer (otherwise referred to as "XMA").

Another type of measurement method using an X-ray micro-analyzer (XMA) and calibration curves will be discussed with reference to FIG. 5, which shows a diagram illustrating the principle of the XMA. The XMA is generally available on the commercial market and operates as follows.

The XMA analyzes a micro-area on the surface of the inspection plate 5 using an X-ray spectrum without destroying the material of the area. Electron beam 13 is emitted from electron gun 12 which is an electro-optical system comprising filament 121, Wehnelt cathode 122, and anode 123. The electron beam 13 is focused on a micro-area of the plate 5 through focusing lens 14 and objective lens 15. Characteristic X-rays 16, inherent to the elements contained in the plate 5, are generated at the spot on plate 5 whereat the electron beam impinges.

The generated X-rays 16 are separated into spectral components by spectroscopic crystal 17 of an X-ray spectrographic system, and are measured with detector 18 for both qualitative and quantitative analyses of the micro-area. The spot being analyzed on plate 5 is accurately determined using an optical microscope. High voltage generating circuit 21 generates a high voltage to accelerate electron beam 13. The accelerating voltage is controlled to be adjustable as desired. Lens coil exciter 22 generates a voltage for exciting focusing lens 14 and objective lens 15. Scanning coil 23 scans the surface of plate 5 with electron beam 13. Electronic scanning circuit 24 drives scanning coil 23. X-ray measurement circuit 25 receives signals from detector 18 and generates a measurement signal which is applied to cathode ray tube 20, pen recorder 26, and typewriter 27. The generated measurement signal corresponds to the values of the quantitative and qualitative results and is based on the output signals from the detector 18. A pen recorder 26 records the output signals from the X-ray measuring circuit 25. The typewriter 27 prints out the results of the signal processing for storage or other purposes , such as use by a computer, for outputs from the X-ray measuring circuit 25.

The system also comprises a vacuum exhaust device 28 for exhausting the system during the times from generation of electron beam 13 to detection by the X-ray.

When electron beam 13 is applied to the corrosion film 3 on plate 5, the specific elements contained in the corrosion film 3 generate inherent characteristic X-rays. By obtaining the spectrum of the generated characteristic X-rays, using analyzing or spectroscopic crystal 17, and by counting the quantity of characteristic X-rays for each element, the identity of the different elements and the percentage of contents can be readily obtained. The XMA thus indicates the ratio of each component element present, such as sulfur, chlorine, etc, which are present as compounds, in terms of measured values, i.e. mass content.

After the mass percentages of compound components, such as sulfur, chlorine, etc, are determined by measuring with the XMA, film 3 is etched using a SIMS, as explained in FIG. 3. These steps are continued until the ion count reaches half of the initial value, and then is stopped. Then, the depth of the etch pit 34 of FIG. 3, i.e. the thickness of corrosion film, is directly measured with a probe. In this manner, the ratio of an element quantity, i.e. the mass content, which is contained, such as sulfur, chlorine, etc, and the thickness of the corrosion film 3, are obtained for each type of metal used as the thin metal film formed as the surface of plate 5, such as silver, copper, etc. Then, a calibration curve, which indicates the relationship between the mass percentage and the corrosion film thickness, is prepared for each compound of the different gas to be expected in the corrosion environment and the metal used in the thin metal film surface of the plate. Thus, from the indication of the XMA for a certain corrosion inspection plate 5, the thickness of the corrosion film can be determined using this calibration curve.

In measuring the corrosion film using the XMA, scanning of the corrosion inspection plate 5 with an electron beam provides accurate measured values without any bias. The invention has significant advantages in that the elements contained in the metalic film and the gas contained in the corrosive environment can be identified without etching of the plate or thin metal film surface, and from the indication of the mass percentage content, an accurate thickness of the corrosion film can be readily and easily obtained.

Figure 6:
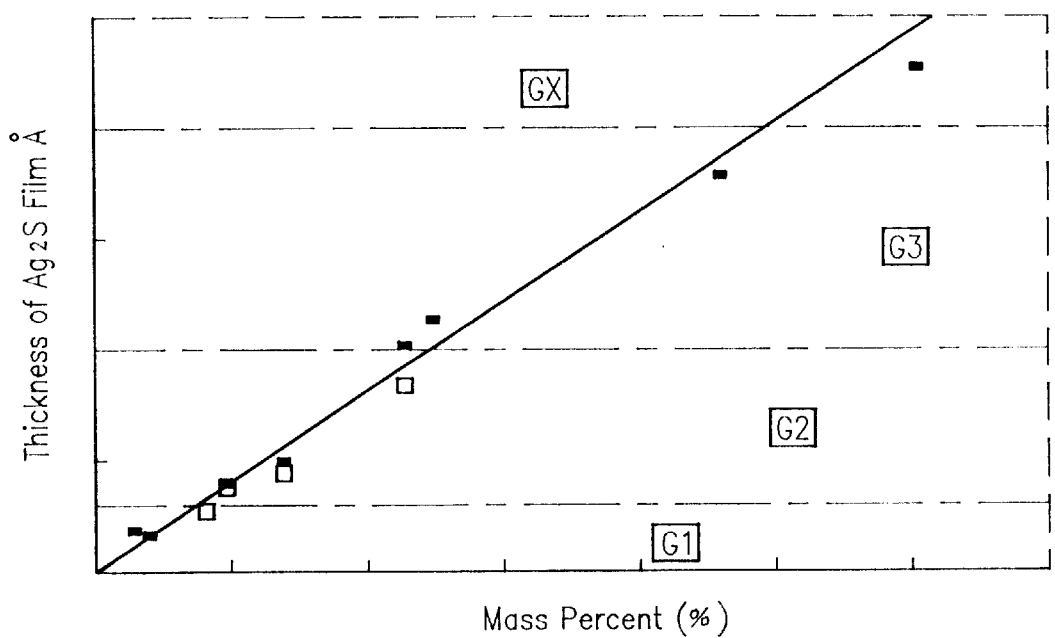
FIG. 6 is a calibration graph depicting the thickness measurement of a thin film of silver sulfide by use of the XMA.

FIG. 6 is a graph of a calibration curve showing the relationship between the sulfur component, contained in silver sulfide, and the thickness of the corrosion film 3 which was measured using the XMA and SIMS in the manner as described. From this graph, the thickness of the corrosion film of silver sulfide corresponding to the percentage mass content indicated by the XMA, can be readily and easily obtained. On the graph, the white squares show measurement by the cathode reduction method, and the black squares indicate measurement by the method of the invention. For all practical purposes, both measurements may be regarded as being in substantial agreement with each other.

Figure 7:
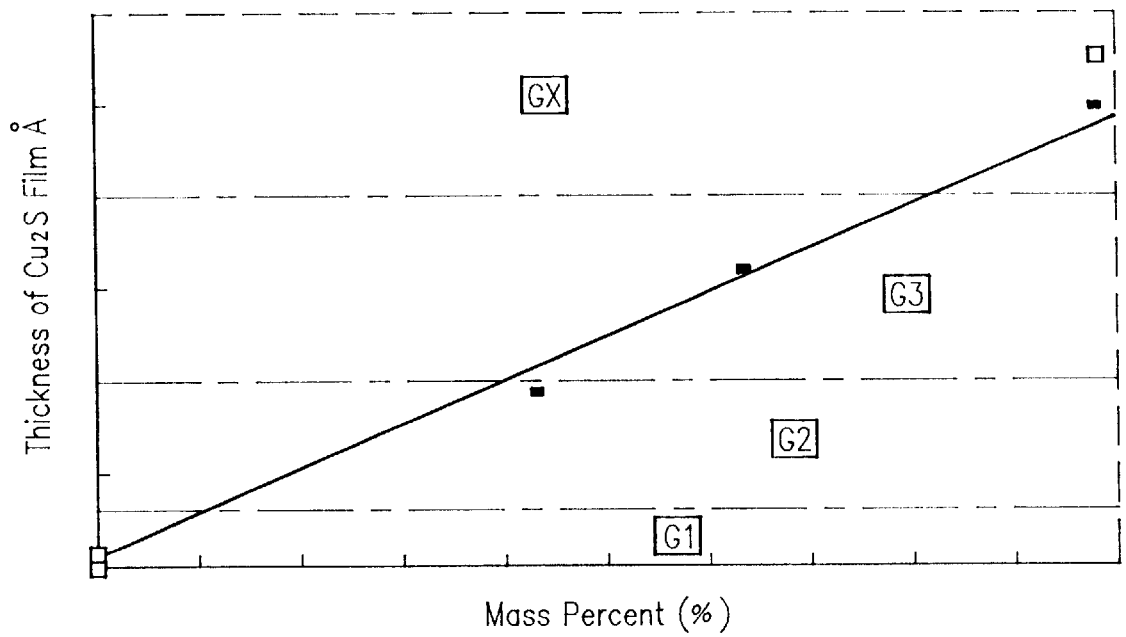
FIG. 7 is a calibration graph depicting the thickness measurement of a thin film of copper sulfide by use of an XMA.

FIG. 7 is a graph of a calibration curve showing the relationship between the sulfur component contained in copper sulfude and the thickness of the corrosion film 3, which was measured in a manner similar to that discussed above using the XMA and SIMS. From the indications of the mass percentage contents by the XMA, the corresponding thickness of the corrosion film can be readily and easily determined.

Figure 8:
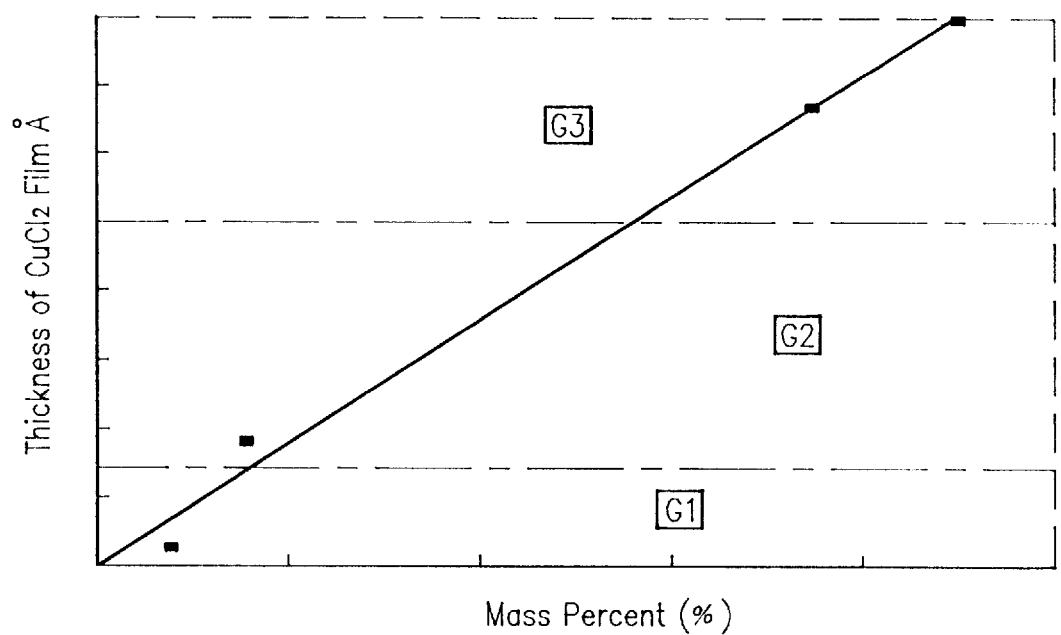
FIG. 8 is a calibration graph depicting the thickness measurement of copper chloride by use of an XMA.

FIG. 8 is a graph of a calibration curve showing the relationship between the chlorine component contained in copper chloride, and the thickness of the corrosion film, which was obtained in a manner similar to that discussed above using the XMA and SIMS. Similarly, the thickness of the corrosion film can be readily and easily obtained.

The thickness of the corrosion film 3 formed on the thin metal film 2 formed on a silicon substrate 1 of the corrosion inspection plate 5 can be measured by using the XMA. The corrosion inspection plate 5, comprising the silicon substrate and thin metal film surface, is exposed for about one month to the corrosive atmospheric environment. The silicon substrate-thin metal film plate has excellent reproducibility, and its corrosion surface is substantially flat so that corrosive action can progress stably.

Next, the corrosion film 3 formed by exposure to the corrosive environment is subjected to quantitative analysis to determine the identity of the compounds of copper, silver, etc with chlorine, sulfure, and oxygen, using the XMA.

To improve measurement sensitivity, the electron acceleration voltage of the XMA is reduced to about 10 kv, which provides high sensitivity to oxygen and carbon. In addition, an area of about 0.15 mm$^2$ of the corrosion film 3 is scanned by the electron beam 13 to prevent localization of the measurement.

The ionic concentration, i.e. mass content, with respect to each element of the corrosion film 3 within the area where the electron beam is irradiated is analyzed. The ionic concentration is compared with a calibration curve, e.g. FIG. 7 for this measurement example, for the same corrosion film that was previously obtained and the thickness of the corrosion film is obtained. Based on this thickness of the corrosion film, the corrosive environment is determined to be of one of the various levels of corrosion severity, namely, G1, G2, G3, or GX, in accordance with the ISA corrosion standard.

By scanning inspection plate 5 with an electron beam using the XMA enables uniform measurement in the selected area. If the calibration curves are stored in a computer, a rapid comparison can be made.

The method of the invention has the following effects and (1) By using an inspection plate 5 having a substantially flat surface and fine surface finish, corrosion proceeds in an uniform manner. Hence dispersion of measurement results is minimized.

(2) The use of the XMA enables quantitative analysis of all elements, except H, He, and Li. Analysis for copper chloride, which cannot be achieved with the conventional cathode reduction method, in now achievable. This has a very significant commercial advantage in that chlorine reacted corrosion is a difficult problem for various engineering components. With the invention, it is now possible to measure such chlorine reacted corrosion.

(3) The cathode reduction method requires a metal plate which is larger than a certain predetermined area in order to ensure measurement accuracy. In the invention, the size of the corrosion inspection plate can be as small as 1×1 mm$^2$.

In practice, and considering the reproducibility of the corrosion measurement process, a 7×7 mm$^2$ plate is used, for example.

(4) Since the invention corrosion inspection plate 5 uses a silicon substrate, which is currently used widely to manufacture integrated circuits, all of the advantages enjoyed by such manufacturing process are enjoyed also by the invention. Also, the cost of manufacturing the invention is low because of the use of the silicon technology.

(5) Although the XMA is expensive, the analysis takes only a short time when using the XMA. Thus, the XMA is suitable for analyzing large quantities of test specimen. Accordingly, the invention further enjoys the advantages of reliability and high speed.

(6) Since the surface of the thin metal film 2 is finished to be substantially flat, observation of its cross section can be done by the use of a transmission electron microscope, which was not previously used in the prior art. In addition, depth profile in the direction of the thickness of the corrosion film 3, can now be readily obtained with the use of an auger analyzer.

A novel casing is provided by the invention for holding the inspection plate 5, so that plate 5 will be disposed at optimum position in a corrosive environment for testing of the gases in environment. FIG. 9 shows an illustrative embodiment of the casing of the invention. The case or casing comprises a base 100 and a cover 200 which when engaged with each other form the casing and hold therein the inspection plate 5.

Figure 22A:
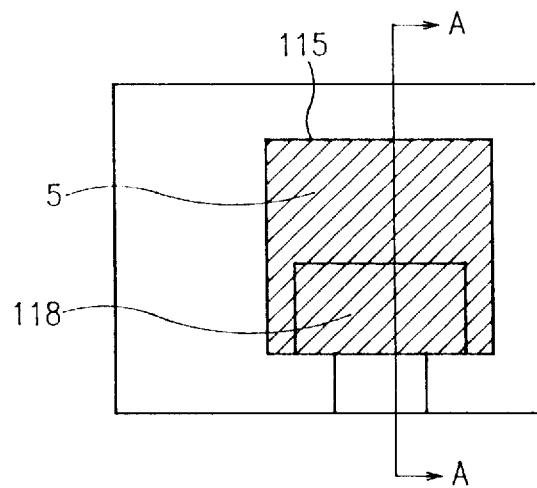
FIGS. 22(a),22(b) and 22(c) are explanatory drawings depicting an enlarged inspection plate support.
Figure 22C:
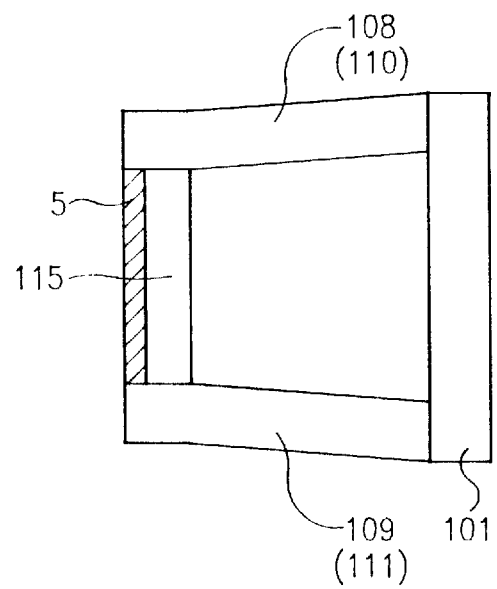
Figure 22B:
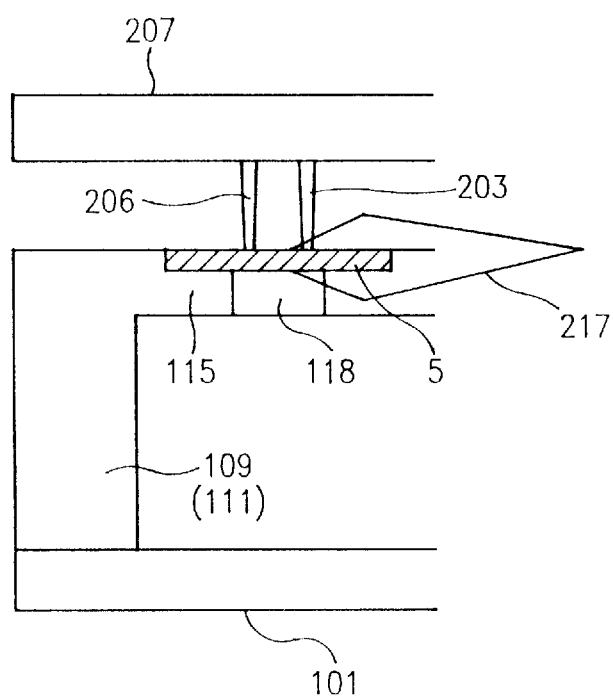

Base 100 comprises bottom plate 101 (see FIG. 22(b), for example), inclined parts 102 (104, in the drawing and specification, the number in parenthesis indicates the counterparts located in the rear), and 103 (105), top part 106, shelf 107 positioned at the center, and supports 108 (110) and 109 (111) holding shelf 107 at four corners being built into one unit. At one end of top part 106, a small hole 112 is provided to exposed the plate to a corrosive environment.

On the upper face of shelf 107, at the center of base 100, there are supports 113,114,115 for holding the corrosion inspection plates (the supports will be henceforth indicated as being "inspection plate supports") provided in a line. In inspection plate supports 113,114,115, there are provided dents which are of suitable size and shape so that corrosion inspection plate 5 are held immobile. On one side of the front of inspection plate supports 113,114,115, notched parts 116,117,118 are provided so that each inspection plate 5 can be taken out by use of an upward force. On each inspection plate support 113,114,115, corrosion inspection plate 5, cut to be of a size approximately 7×7 mm$^2$, is placed. Although three inspection plate supports 113,114,115 are shown in the drawing, the number of supports can be increased as desired if the number of plates 5 is increased.

In inclined parts 102 (104) and 103 (105), joint openings 119 (121) and 120 (122) are provided so that fixing paws 208 (210) and 209 (211), which are part of cover 200, are moved into connection openings 119–122 from top part 106 to secure cover 200 to base 100. An arrow 123 indicates that gases in the corrosion environment flow in a direction parallel to the top part 106.

Cover 200 comprises top board part 207 having a plurality of holding bars 201–206 to press corrosion inspection plate 5 in the back thereof, inclined parts 212 (214) and 213 (215) supporting the top board part 207, and fixing paws 208–211 located in part of the inclined parts 212–215 and all of these components being integrated into cover 200 as one unit. Cover 200 is supported thereon by top art 106. By pushing fixing paws 208–211,integrated into cover 200, into joint openings 119–122 of base 100 from each corresponding position of top part 106, cover 200 and base 100 are mutually engaged. Simultaneously, inspection plates 5, placed on inspection plate supports 113,114,115, are also secured by pressing such supports with holding bars 201–206. Arrow 216 indicates the the direction of gas flow in the direction parallel to the drawing surface in both base 100 and cover 200. The base, cover, and other members may be made of a transparent acrylic resin which is substantially free of gas absorption.

FIG. 10 shows a side view of the casing assembly with the front, rear, top and bottom viewing directions of the casing being shown by the arrows. FIGS. 11,12,13, and 14 are views of the case taken from such viewing directions.

FIG. 11 shows the top view of the case. By pushing fixing paws 208–211, provided at four locations in cover 200,into joint openings 199–122 of base 100 from each corresponding position on top part 106, cover 200 and base 100 are mutually engaged.

Figure 12:
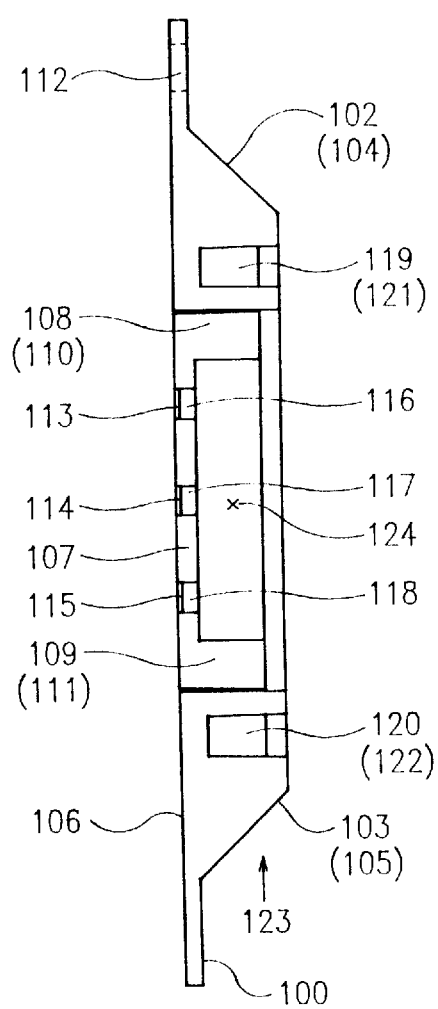
FIG. 12 is a front view depicting the illustrative casing.

FIG. 12 shows the front view of base 100 of the case. On shelf 107, provided nearly at the center of top part 106, there is provided a plurality of inspection plate supports 1113,114, 115 which allow the plates 5 to be seated so as to be substantially immobile, and the four corners of the series of inspection support plates 113–115 are held by posts 108 (110) and 109 (111) on the bottom board 101. On a side of the front of inspection plate supports 113–115, notched parts 116–118 are provided, so that each plate can be taken out by moving same upward.

Figure 13:
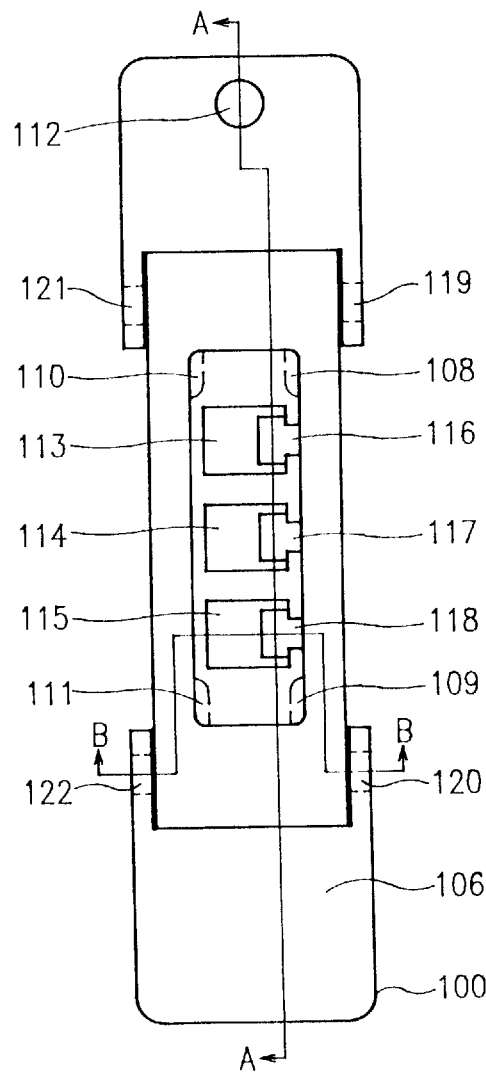
FIG. 13 is a top view depicting the illustrative casing.

FIG. 13 shows the top view of base 100 of the case. This part appears for viewing when cover 200 is removed. Inspection plate supports 113–115 are sunk to make a dent, into which plates 5 are seated so that the plates 5 do not move. Notched parts 116–118 are provided to facilitate installation and removal of the plates which rest on inspection plate supports 113–115, by holding the top and bottom edges of the plates with a pair of tweezers, for example. The part is discussed in further detail with reference to FIG. 14. Posts 108–111 hold shelf 107, on which inspection plate supports 113–115 are placed in a line on bottom board 101. By pushing fixing paws 208–211, provided on cover 200, into joint openings 119–122 of base 100, each at its respective position, cover 200 is engaged with base 100.

Figure 14:
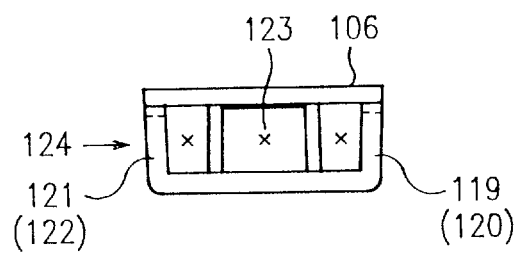
FIG. 14 is a side view depicting the base of the casing of FIG. 13.

FIG. 14 shows a side view of base 100, wherein top part 106 of base 100 is shown. When fixing paws 208–211 on cover 200 are pushed into the joint openings 199–122, each at its corresponding position, base 100 engages cover 200. The direction perpendicular to the surface of the drawing is shown by an X 123, and the direction shown by arrow 124 are the directions in which the corrosive gas flows.

Figure 15:
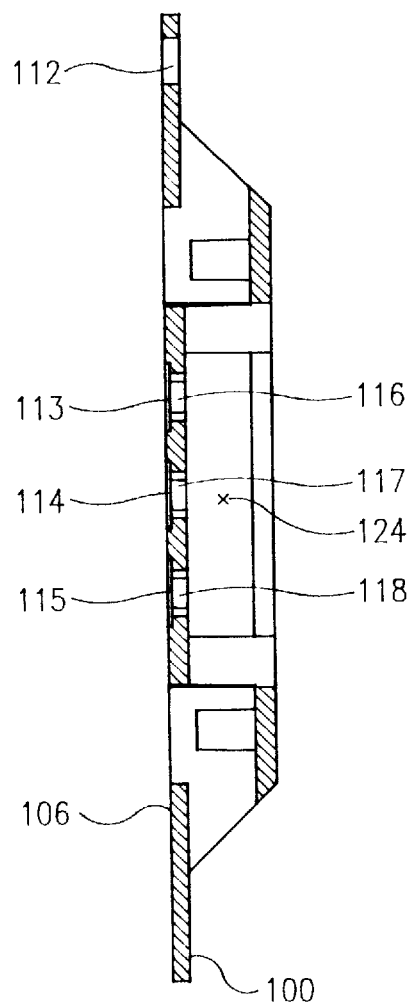
FIG. 15 is a cross sectional view taken along section line A—A of the base of FIG. 13.

FIG. 15 shows a cross sectional view taken along section line A—A in FIG. 13, wherein X 124 indicates the direction of gas flow which is perpendicular to the drawing surface. Provided are inspection plate supports 113–115, and notched parts 116–118 for removing plates 5. X marks the direction of gas flow.

Figure 16:
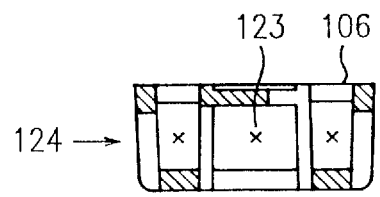
FIG. 16 is a cross sectional view taken along section line B—B of the base of the casing of FIG. 13.

FIG. 16 shows a cross sectional view taken along section line B—B in FIG. 13. wherein X 123 indicates the direction perpendicular to the drawing surface, and in which direction gas flows. Also, arrow 124 indicates the direction of gas flow.

Figure 17:
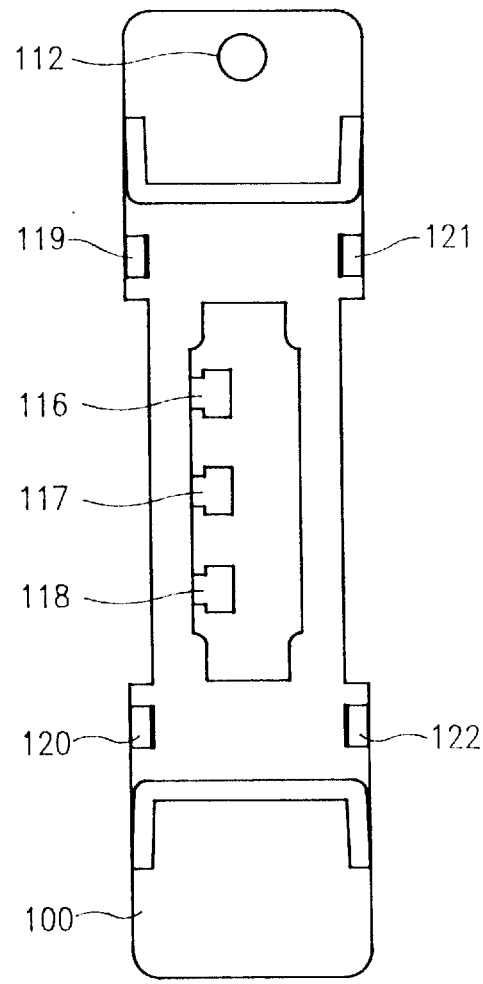
FIG. 17 is a bottom view depicting the base of the illustrative casing.

FIG. 17 shows the bottom view of base 100, where notched parts 116–118 are provided. When fixing paws 208–211, provided on cover 200, are pushed into the joint openings 199–122, each at its respective position, base 100 engages cover 200.

FIG. 18 shows the front view of cover 200, wherein holding bars 201–206 are integrated in cover 200 to press plates 5. Holding bars 201–206 are installed at such positions that, when fixing paws 208–211 on cover 200 are pushed down into the joint openings 199–122 from top part 106, the holding bars come into positions where they press plates 5 to rest on inspection plate supports 113–115. Fixing paws 208–211 are bent slightly inward when they are pushed into the joint openings 199–122 from top part 106, before cover 200 is finally engaged with base 100. FIG. 20 shows with double headed arrows the directions in which the fixing paws are bent. The gas flows in directions 124 and 216, as discussed with reference to FIG. 12.

FIG. 19 shows the top view of cover 200. At the rear thereof holding bars 201–206 are installed to press the plates 5. At the front and rear of both ends of cover 200, there are fixing paws 208–211 that are pushed into base 100, each at its respective position, to engage cover 200. The gas flows in directions 124 and 216 in the environment as discussed in FIG. 9.

FIG. 20 shows a side view of cover 200. Fixing paws 208–211, shown in FIG. 9, are bent inward when cover 200 is pushed to engage base 100. The fixing paws return to their normal positions when cover 200 is pushed all the way to the end with cover 200 engaged with base 100. To remove cover 200, paws 208–211 are pressed from the outside to the inside to pull cover 200 out of engagement with base 100. The directions of gas flow are as explained in FIG. 9.

FIG. 21 shows the bottom rear view of cover 200, wherein holding bars 201–204 used for holding plates 5 are installed on cover 200. The holding bars press plates 5, placed on support 113. Similarly, holding bars 202, and 205, and 203 and 206 press plates 5 provided on supports 114, and 115, each at its respective position. The directions of gas flow are as explained in FIG. 9.

The process of installing and removing the plates 5 from the casing is hereinafter discussed in greater detail with reference to FIGS. 22(*a*)–22(*c*). In FIG. 9, by pressing fixing paws 208–211 from the outside to the inside, the fixing paws are disengaged from base 100, and cover 200 can be moved upward. Then, the upper face of inspection plate supports 113–115, as shown in FIG. 13, appears. FIGS. 22(*a*)–22(*c*) are enlargements of the area around, for example, inspection plate support 115, which is one of the supports at the left end.

The shaded part in FIG. 22(*a*) shows plate 5. The drawing shows the state wherein the inspection plate 5 rests on a dent, which is provided so that plate 5 is held immovable on the inspection plate support. Since a notched part 118 is provided at a part of inspection plate support 115, plate 5 can be held with a pair of tweezers 217 at the top and bottom edges thereof.

FIG. 22(*b*) is an enlargement of the front portion of FIG. 22(*a*). When cover 200, inspection plate 5, and base 100, are assembled, plate 5 which is placed on inspection plate support 115 is fixed securely, so as to not fall off, with holding bars 205, 206, being provided at the rear of top board 207. When cover 200 is removed, since holding bars 205, 205 are not disposed therein, plate 5 resting on the notched part 118, can be easily pulled up by picking up the plate at its upper and lower edges with a pair of tweezers 217.

FIG. 22(*c*) is a side view of FIG. 21(*a*). The left edge of support 115 is supported by posts 109,111 on bottom plate 101.

The case or casing of the invention has many advantages and features. For example, by placing the inspection plate 5 on the support (e.g. 113), provided on the upper surface of base 100, and by simple use of a pair of tweezers 217, the following can be readily accomplished: (a) By simply pushing down the fixing paws of the cover aligned with a predetermined position, the plate 5 can be securely held in a position between the base 100 and cover 200; (b) Simultaneously, the base 100 and cover 200 can be mutually engaged; (c) The cover 200 can be easily removed by simply pressing the fixing paws inwardly; and (d) The inspection plates 5 can be easily removed from the supports by merely using the tweezers.

Advantageously, the invention is suitably provided with excellent ventilation so that gases in the corrosive atmosphere being tested can freely flow above the plates 5. Also, air flow passages are strategically placed to prevent occurrence of harmful whirls which interfere with natual air flow. Since the top board of the cover protects plate 5 from settling dust and direct rainfall, corrosion progresses in a stable steady manner, which enables a more accurate reading.

The foregoing description is illustrative of the principles of the invention. Many extensions and modifications thereof would be apparent to the worker skilled in the art. All such extensions and modifications are to be considered to be within the spirit and scope of the invention.

What is claimed is:

1. In a corrosion inspection apparatus comprising a corrosion inspection plate having a surface which forms a corrosion film when exposed to a corrosive environment, means for holding said corrosion inspection plate, and means for measuring the depth of said corrosion film formed on said surface of said corrosion inspection plate; the improvement comprising:

said corrosion inspection plate consisting of a metal film of copper or silver formed by sputtering or vacuum deposition on an entire surface of a flat silicon substrate and at a temperature which enables the surface of said metallic film which is exposed to the corrosive environment to have a constant roughness value which is 10% or less than the thickness of said metallic film; and said means for measuring comprises:
a secondary ion mass spectrometer for counting secondary ions of a compound formed by the corrosive environment acting on said metallic film surface per unit time;
means for storing data of secondary ion counts per unit time for different compounds formed by the corrosive environment; and
means for comparing the detected ion count per unit time with the stored data of ion count per unit time for the different compounds thereby to determine the depth of said corrosive film and type of compound formed by the corrosive environment; wherein said means for holding comprises:
a base for accommodating said corrosion inspection plate, said base comprising:
shelf means attached to a corner of said base; and
a plurality of support means attached to said shelf means for holding said corrosion inspection plate; and
a cover removably attached to said base, said cover comprising fixing paw means for interconnecting said cover to said base.

2. The plate of claim 1, wherein said silicon is of p-type and has a specific resistance of between 4 to 20 cm.

3. The plate of claim 1, wherein said corrosion environment produces an oxide at a surface of said metallic film.

4. The plate of claim 1, wherein said corrosion environment produces a chloride at a surface of said metallic film.

5. The plate of claim 1, wherein said corrosion environment produces a sulfide at a surface of said metallic film.

* * * * *